US00PP08767P

United States Patent [19]

Zary

[11] Patent Number: Plant 8,767

[45] Date of Patent: Jun. 7, 1994

[54] HYBRID TEA ROSE PLANT NAMED 'JACFRUIT'

[75] Inventor: Keith W. Zary, Thousand Oaks, Calif.

[73] Assignee: Bear Creek Gardens, Inc., Medford, Oreg.

[21] Appl. No.: 42,496

[22] Filed: Apr. 2, 1993

[51] Int. Cl.[5] ..... A01H 5/00

[52] U.S. Cl. ..... Plt./18

[58] Field of Search ..... Plt. 11, 15, 18, 22, Plt. 26

*Primary Examiner*—Howard J. Locker

*Attorney, Agent, or Firm*—Klarquist Sparkman Campbell Leigh & Whinston

[57] ABSTRACT

A hybrid tea rose having distinctive, old-fashioned flower form; very strong, citrus flower fragrance; upright, vigorous growth habit; and seven leaflet leaves.

1 Drawing Sheet

The present invention relates to a new and distinct variety of rose plant of the hybrid tea class which was originated by me by crossing the variety JAColite, U.S. Plant Pat. No. 4,167, with the variety JACdis, U.S. Plant Pat. No. 3,423.

The primary objective of this breeding was to produce a new rose variety having the upright growth habit and vigor of the female parent, JAColite, combined with the very heavy scent of the male parent. The objective was substantially achieved along with other desirable improvements as evidenced by the following unique combination of characteristics which are outstanding in the new variety and which distinguish it from its parents, as well as from all other varieties of which I am aware:

1. Old-fashioned hybrid tea flower form;
2. Distinctive, strong, citrus (grapefruit) fragrance;
3. Vigorous, upright growth; and
4. Presence of seven leaflet leaves.

Asexual reproduction of this new variety by budding, as performed at Wasco, Calif., shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with the Royal Horticultural Society (London) Colour Chart, except where ordinary dictionary significance of color is indicated.

Parentage:

*Seed parent.*—JAColite, U.S. Plant Pat. No. 4,167.

*Pollen parent.*—JACdis, U.S. Plant Pat. No. 3,423.

Classification:

*Botanical.*—Rosa hybrida.

*Commercial.*—Hybrid tea.

FLOWER

Observations made from specimens grown in a garden environment in Somis, Calif., from April through November, 1992.

Blooming habit: Recurrent.

Bud:

*Size.*—1¾ inches when the petals start to unfurl.

*Form.*—Long, pointed ovoid to globular.

*Color.*—When sepals first divide, bud color is White Group 155D with a pink cast on the petal edges (Red Group 49D). When half blown, the upper sides of the outer petals are White Group 155D with inner petals Red Group 49C; and the lower sides of the petals are White Group 155D.

*Sepals.*—Color: Green Group 146B. Surface texture: Covered in fine hairs. There are three normally to heavily appendaged sepals. There are two unappendaged sepals with hairy edges.

*Receptacle.*—Color: Green Group 137C. Shape: Funnel. Size: Broad (⅜×2/8 inch). Surface: Smooth.

*Peduncle.*—Length: Medium (3 inches). Surface: Glandular. Color: Light green and bronzy. Strength: Stiff, erect.

Bloom

*Size.*—Large. Average open size is 4½ inches.

*Borne.*—Singly.

*Stems.*—Long (16–20 inches), strong.

*Form.*—When first open: High centered. Permanence: All petals curl.

*Petalage.*—Number of petals under normal conditions: 35–40.

*Color.*—The upper side of the petals is White Group 155D on the outer petals; Red Group 49D on the inner petals. The reverse side of the petals is White Group 155D. The base of each petal has a greenish yellow half moon (⅜×⅜ inch) at the point of attachment. The major color on the upper side is Red Group 49D.

*Variegations.*—None.

*Discoloration.*—The general tonality at the end of the first day: No change. At the end of the third day: As the flower ages, the pink fades, to be replaced by white.

*Fragrance.*—Strong, distinctive citrus (grapefruit) fragrance.

Petals:

*Texture.*—Thin.

*Shape.*—Oval.

*Form.*—Tips slightly recurved, edges slightly quilled.

*Arrangement.*—Irregular, with many petaloids in the center.

*Persistence.*—Drop off cleanly.

*Lastingness.*—On the plant: Long (5 days). As a cut flower: Long (7 days).

Reproductive parts:

*Anthers.*—Size: Medium. Quantity: Many. Color: Yellow. Arrangement: Regular around styles, mixed with petaloids.

*Filaments.*—Color: Reddish brown.

*Pollen.*—Color: Lemon yellow.

*Styles.*—Color: White.

*Stigmas.*—Color: Red.

Form: Bush.

Growth: Vigorous, upright, branching.

Foliage: Number of leaflets on normal mid-stem leaves: 5 or 7, but more 7 leaflets than normal.

*Size.*—Large (6×4 inches).

*Quantity.*—Abundant.

*Color.*—New foliage: Reddish. Old foliage: Dark green, semi-glossy.

Leaflets:

*Shape.*—Pointed oval.

*Texture.*—Upper side: Leathery.

*Edge.*—Serrated.

*Serration.*—Single, small.

*Petiole rachis.*—Color: Green.

*Petiole underside.*—Rough, with prickles.

*Stipules.*—Medium, serrated, bearded.

*Disease resistance.*—Susceptible to mildew but resistant to rust under normal growing conditions at Somis, Calif.

Wood:

*New wood.*—Color: Light green. Bark: Smooth.

*Old wood.*—Color: Green. Bark: Smooth.

Prickles:

*Quantity.*—On main canes from base: Many. On laterals from main canes: Ordinary.

*Form.*—Medium ($\frac{3}{8}$ inch), straight.

*Color when young.*—Red.

Small Prickles:

*Quantity.*—On main stalks: Few. On laterals: Many.

*Color.*—Green.

I claim:

1. A new and distinct variety of rose plant of the hybrid tea class, substantially as herein shown and described, characterized particularly as to novelty by the unique combination of its distinctive, old-fashioned flower form; very strong, citrus flower fragrance; upright, vigorous growth habit; and seven leaflet leaves.

* * * * *

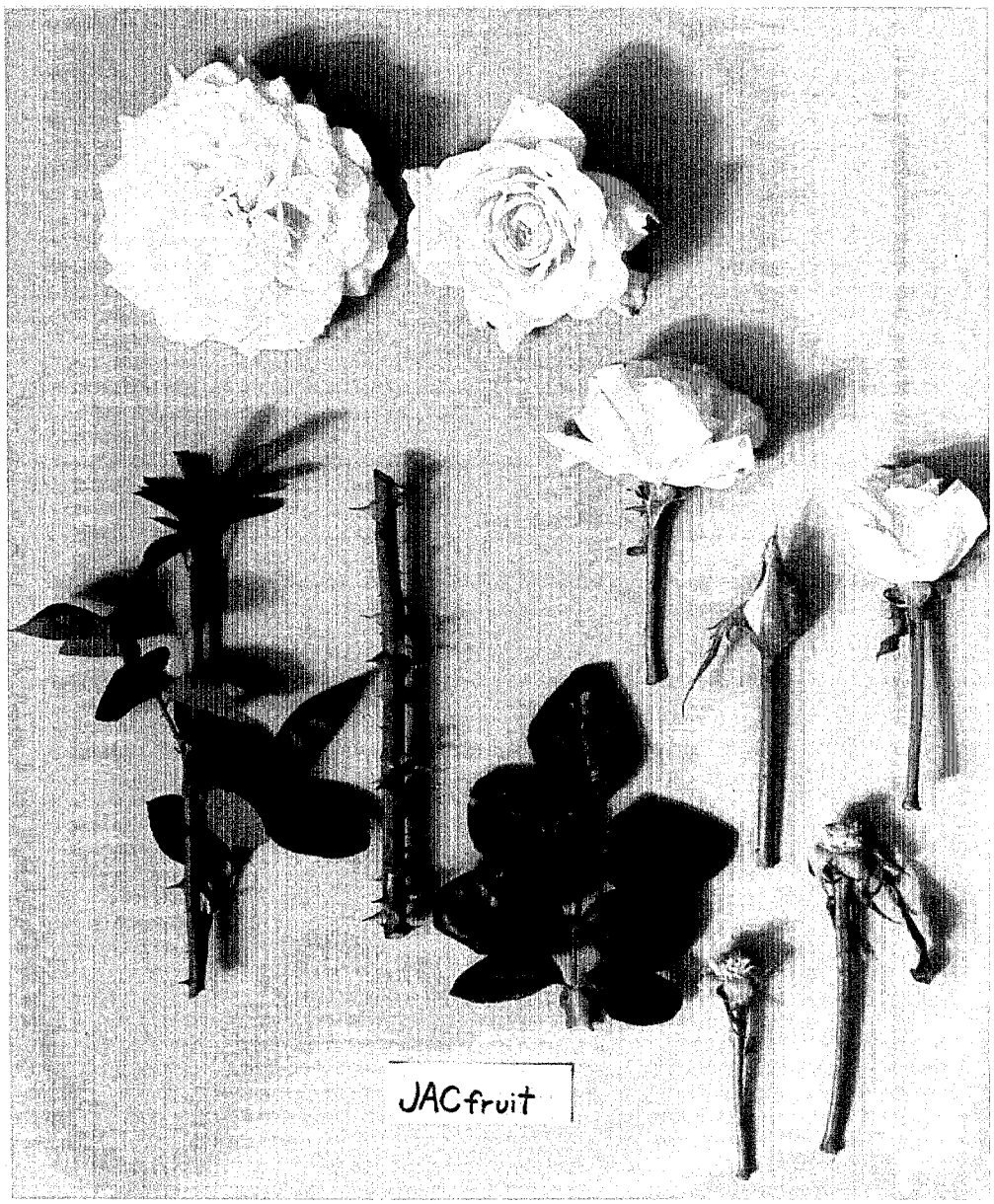
JACfruit